(12) United States Patent
Everman et al.

(10) Patent No.: US 11,172,845 B1
(45) Date of Patent: Nov. 16, 2021

(54) COMBINED EXHALED AIR AND ENVIRONMENTAL GAS SENSOR APPARATUS

(71) Applicant: GMECI, LLC, Beavercreek, OH (US)

(72) Inventors: Bradford R Everman, Haddonfield, NJ (US); Brian Scott Bradke, Brookfield, VT (US)

(73) Assignee: SPOTLIGHT LABS, Haddonfield, NJ (US)

( * ) Notice: Subject to any disclaimer, the term of this patent is extended or adjusted under 35 U.S.C. 154(b) by 0 days.

(21) Appl. No.: 16/933,680

(22) Filed: Jul. 20, 2020

(51) Int. Cl.
  *A61B 5/083* (2006.01)
  *G01N 33/497* (2006.01)
  *A61B 5/00* (2006.01)

(52) U.S. Cl.
  CPC .............. *A61B 5/0836* (2013.01); *A61B 5/48* (2013.01); *A61B 5/6803* (2013.01); *A61B 5/746* (2013.01); *G01N 33/497* (2013.01); *A61B 2560/0223* (2013.01); *A61B 2560/0242* (2013.01); *A61B 2560/0247* (2013.01); *A61B 2560/0252* (2013.01); *A61B 2560/0257* (2013.01); *A61B 2562/029* (2013.01)

(58) Field of Classification Search
  CPC ...... A61B 5/6803; A61B 5/082; A61B 5/0836
  See application file for complete search history.

(56) References Cited

U.S. PATENT DOCUMENTS 5,551,419 A * 9/1996 Froehlich ............ A61M 16/024
                                                   128/204.23
6,498,942 B1   12/2002 Esenaliev
10,561,863 B1 *  2/2020 Dashevsky ........ A61B 5/14542
(Continued)

FOREIGN PATENT DOCUMENTS

| KR | 1020050005661 A | 1/2005 |
| WO | 0110295 A1 | 2/2001 |
| WO | 2011104888 A1 | 9/2011 |

OTHER PUBLICATIONS

"Carbon Dioxide Sensor." Dec. 7, 2019. https://web.archive.org/web/20191207003359/https://en.wikipedia.org/wiki/Carbon_dioxide_sensor (Year: 2019).*

(Continued)

*Primary Examiner* — Meredith Weare
(74) *Attorney, Agent, or Firm* — Caldwell Intellectual Property Law, LLC (57) ABSTRACT

A combined exhaled air and environmental gas sensor apparatus for mobile respiratory equipment includes a housing, wherein the housing includes a port aperture, a connector configured to attach the port aperture to a respiratory exhaust port, and at least an ambient aperture connecting to an exterior environment, a sensor positioned within the housing, the sensor configured to detect a carbon dioxide level and generate sensor outputs indicating detected carbon dioxide level, a processor communicatively connected to the sensor, the processor including a memory, a breath analysis mode and an environmental analysis mode, wherein the processor is configured to receive a plurality of sensor outputs from the sensor, match the plurality of sensor outputs to mode parameter profile, and switch between the breath analysis mode and the environmental analysis mode as a function of the mode parameter profile.

20 Claims, 6 Drawing Sheets

(56) References Cited

U.S. PATENT DOCUMENTS

| | | | | |
|---|---|---|---|---|
| 2011/0017211 A1* | 1/2011 | Ahlmen | .............. | A61M 16/104 |
| | | | | 128/203.14 |
| 2012/0330161 A1* | 12/2012 | Kobayashi | ........... | A61B 5/0075 |
| | | | | 600/476 |
| 2017/0160221 A1* | 6/2017 | Savoy | ................ | G01N 33/0008 |
| 2017/0303823 A1* | 10/2017 | Allsworth | ............ | A61B 5/6803 |
| 2017/0323550 A1* | 11/2017 | Patil | .................. | H04M 1/72569 |
| 2018/0333101 A1* | 11/2018 | DeBates | .............. | A61B 5/6898 |
| 2018/0346130 A1* | 12/2018 | Jouper | ............... | G01N 33/0047 |
| 2019/0254565 A1* | 8/2019 | Toth | ..................... | A61B 5/6823 |
| 2020/0215361 A1* | 7/2020 | Delprat | ................. | B64D 11/00 |

OTHER PUBLICATIONS https://learn.adafruit.com/adafruit-sgp30-gas-tvoc-eco2-mox-sensor.

\* cited by examiner

COMBINED EXHALED AIR AND ENVIRONMENTAL GAS SENSOR APPARATUS

FIELD OF THE INVENTION

The present invention generally relates to the field of physiological sensing devices. In particular, the present invention is directed to a combined exhaled air and environmental gas sensor apparatus.

BACKGROUND

Field equipment respiration equipment for pilots, firefighters, and the like is essential for safety and effective performance. Both systems and operators thereof could benefit from accurate sensor feedback. Unfortunately, existent sensors do not account well for the various kinds of information about the wearer and environment in an efficient or effective manner.

SUMMARY OF THE DISCLOSURE

In an aspect, a combined exhaled air and environmental gas sensor apparatus for mobile respiratory equipment includes a housing, wherein the housing includes a port aperture, a connector configured to attach the port aperture to a respiratory exhaust port, and at least an ambient aperture connecting to an exterior environment, a sensor positioned within the housing, the sensor configured to detect a carbon dioxide level and generate sensor outputs indicating detected carbon dioxide level, a processor communicatively connected to the sensor, the processor including a memory, a breath analysis mode and an environmental analysis mode, wherein the processor is configured to receive a plurality of sensor outputs from the sensor, match the plurality of sensor outputs to mode parameter profile, and switch between the breath analysis mode and the environmental analysis mode as a function of the mode parameter profile.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments of the disclosed apparatus use a sensor placed at an exhaust port of a field breathing apparatus to detect and analyze gas composition information both from user exhalations and surrounding environment. Apertures connected to air surrounding the field breathing apparatus permit escape of exhaled air, which may be measured by a sensor within apparatus; subsequently, environmental air may enter apertures, permitting measurement of environmental parameters. Breath patterns and gas composition may be used to assess a physiological state of a user, while carbon dioxide and/or other materials in the surrounding air may be analyzed to detect potential hazards or to warn a user if use of the field breathing apparatus is needed, for instance if the user is not currently wearing the field breathing apparatus.

Figure 1:
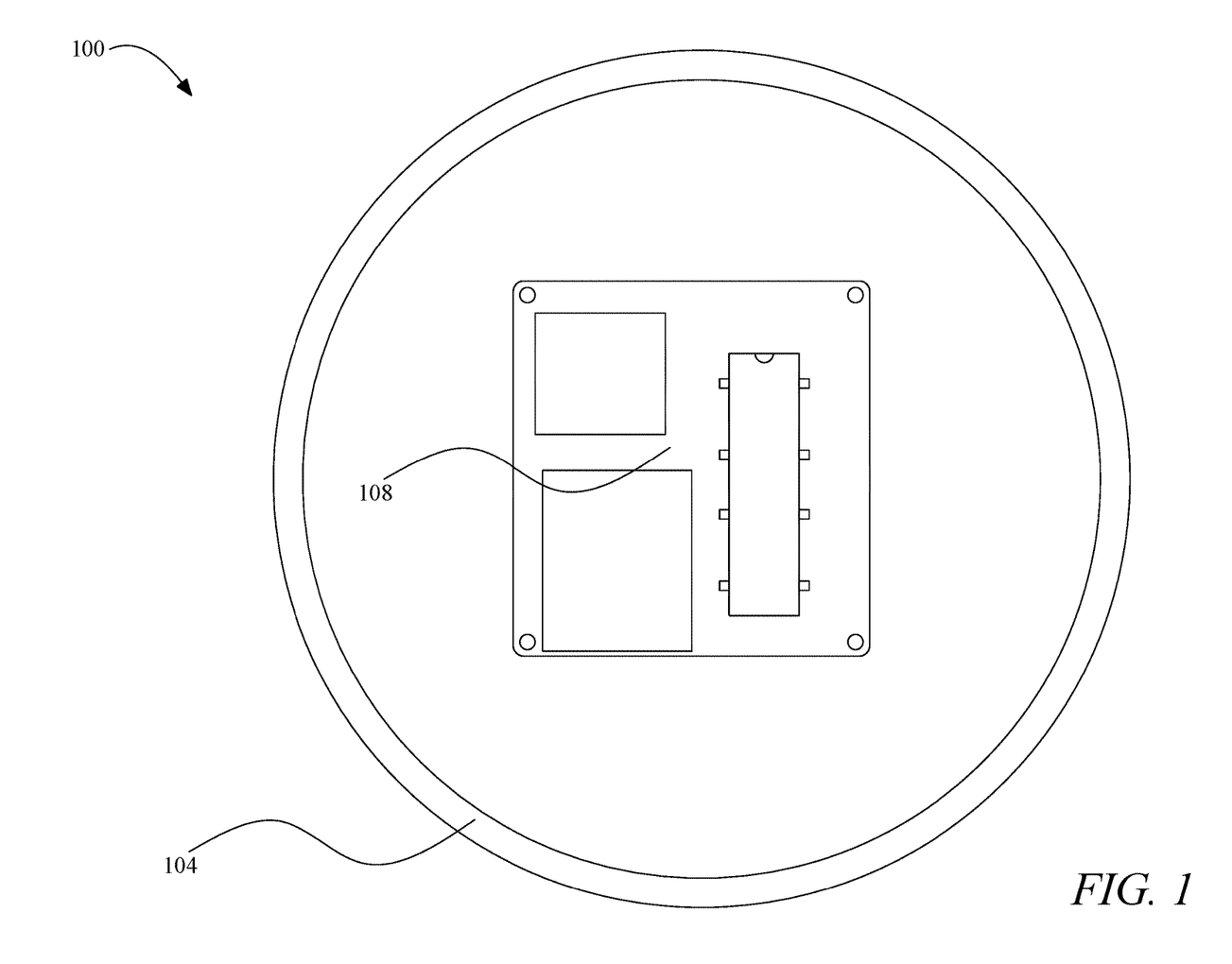
FIG. 1 is a schematic diagram illustrating an exemplary embodiment of a combined exhaled air and environmental gas sensor apparatus.

Referring now to FIG. 1, combined exhaled air and environmental gas sensor 108 apparatus 100 for mobile respiratory equipment is illustrated. Apparatus 100 includes a housing 104, within which one or more electronic components are positioned. One or more electric components include a sensor 108.

Still referring to FIG. 1, housing 104 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 104 may be manufactured in any suitable process including molding such as injection molding, additive manufacturing such as "three-dimensional printing" and/or stereolithography, subtractive processes such as machining, and/or any other process or combination of processes. Housing 104 may include a sensor-bearing surface 112 on or to which one or more electrical components including sensor 108 may be attached. Sensor-bearing surface 112 may be positioned opposite a port aperture as described in further detail below.

Figure 2A:
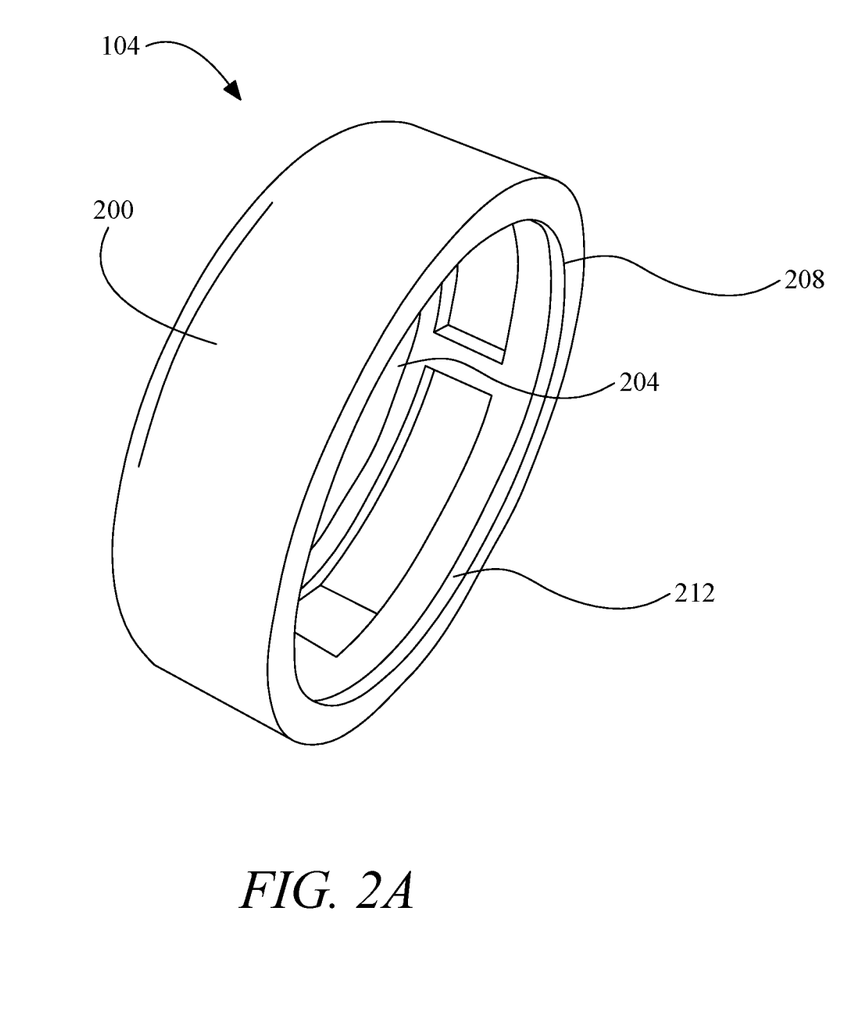
FIG. 2A is a schematic diagram illustrating an exemplary embodiment of a housing.

Referring now to FIG. 2A, a perspective view of an exemplary embodiment of a housing 104 is illustrated. Housing 104 may include an exterior surface 200, an interior surface 204, an interior space surrounded by interior surface 204, and one or more apertures. Housing 104 may have any suitable shape, including a shape of a cap to be placed over a respiratory exhaust port as described in further detail below. Housing 104 may be substantially cylindrical and may have one or more rounded edges. Housing 104 includes a port aperture 208. Port aperture 208 is an aperture that receives exhaled breath from a respiratory exhaust port as described in further detail below, admitting the exhaled breath into interior space of housing 104. Housing 104 further includes a connector 212, which may be located at port aperture 208. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 212 is configured to attach port aperture 208 to exhaust port. Connector 212 may include, without limitation, a rim that fits and/or snaps over a feature of exhaust port to affix port aperture 208 thereto; connector 212 may alternatively or additionally include fastener, such as a bold or screw that inserts through a hole in housing 104 and screws into a reciprocally threaded hole in exhaust port. Connector 212 may include threading around port aperture 208 that engages reciprocal threading at exhaust port. Connector 212 may include and/or be combined with adhesives, sealants, or the like. Connector 212 may permit repeated detachment and reattachment or may effect a permanent connection between port aperture 208 and exhaust port. Persons skilled in the art, upon reviewing the entirety of this disclosure, will be aware of various alternative or additional structures and/or components that may be used for connector 212. Port aperture 208 may be located opposite sensor-bearing surface 112; for instance, sensor-bearing surface 112 may be located on interior surface 204 at a distal end of housing 104, while port aperture 208 may be located at a proximal end of housing 104.

Figure 2B:
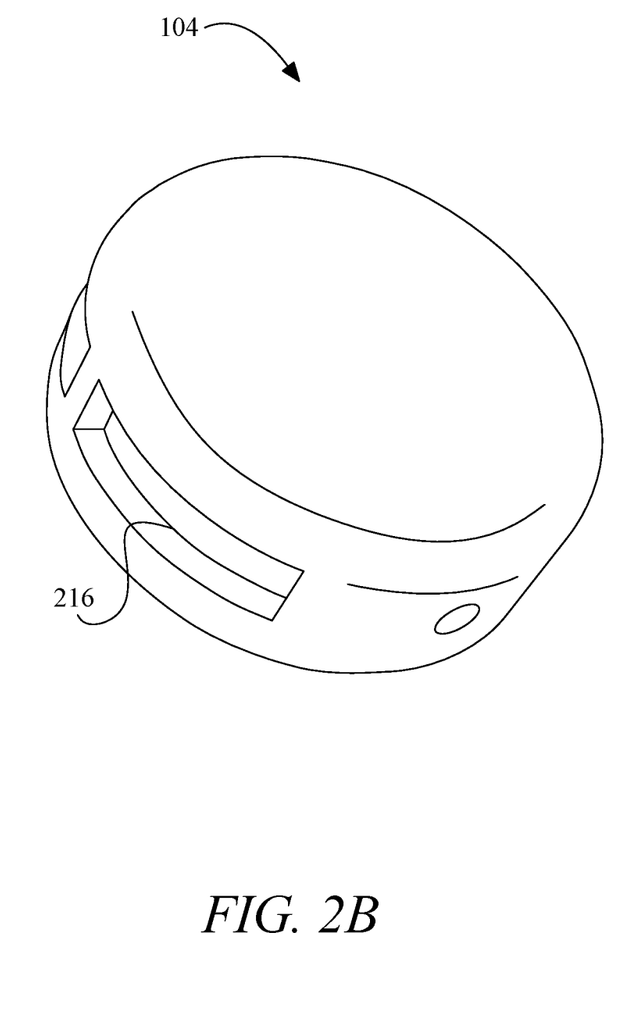
FIG. 2B is a schematic diagram illustrating an exemplary embodiment of a housing.

Referring now to FIG. 2B, housing 104 includes at least an ambient aperture 216 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 216 includes an opening connecting interior space to exterior environment. At least an ambient aperture 216 may permit air to travel freely between interior space and exterior environment.

Figure 3:
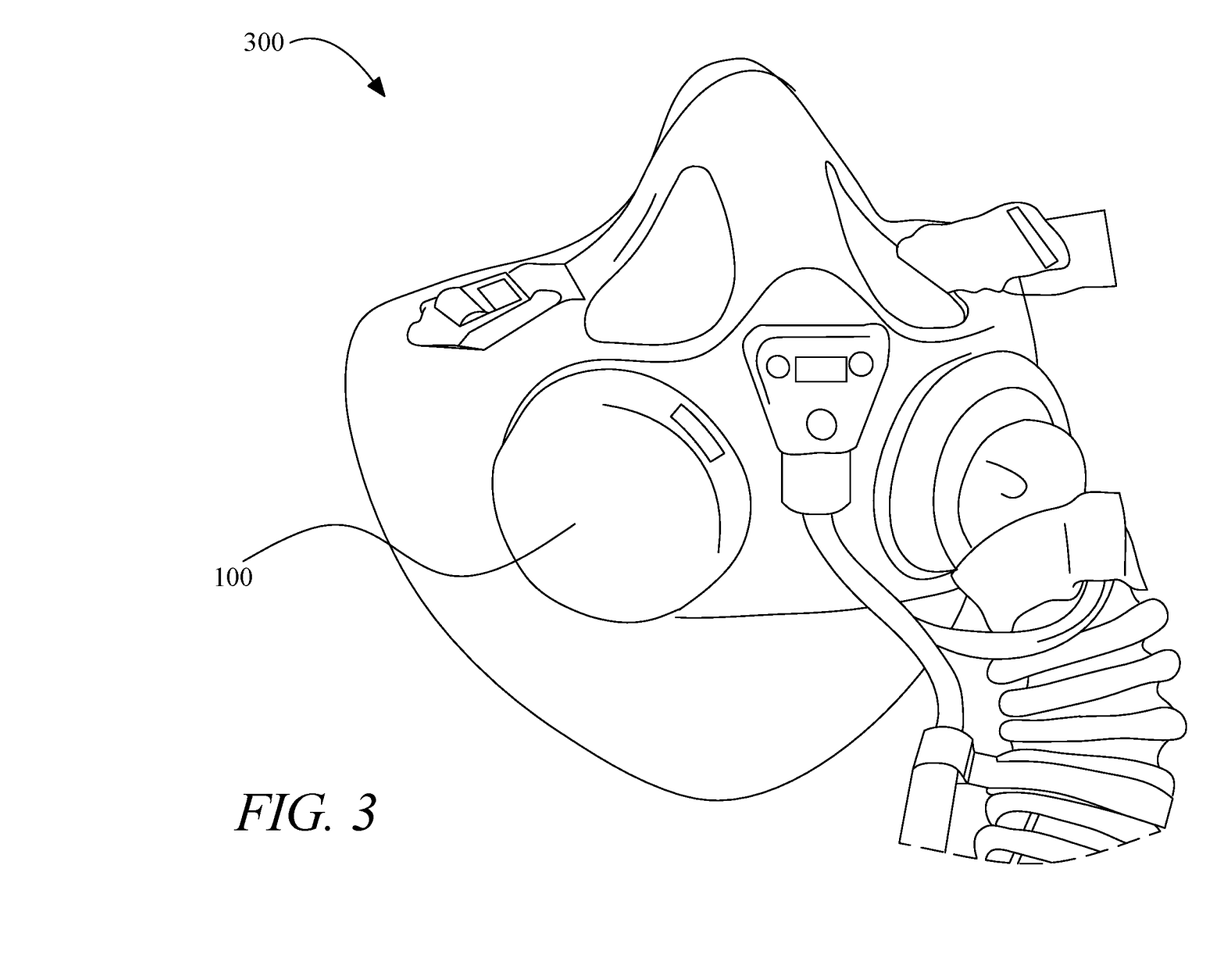
FIG. 3 is a schematic diagram illustrating an exemplary embodiment of a combined exhaled air and environmental gas sensor apparatus.

In an embodiment, and referring now to FIG. 3, housing 104 may be attached to an exhaust port of a mobile respiratory device 300. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or Still referring to FIG. 3, mobile respiratory device 300 may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 3, an "exhaust port," as used in this disclosure, is an outlet that permits air exhaled by a user to escape from a mobile respiratory device 300. Exhaust port may include a valve such as a check-valve or other one-way valve to prevent air from entering a mobile respiratory device 300 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port. In operation, housing 104 with port aperture 208 and ambient aperture 216 may form a plenum in which exhaled and ambient air may flow freely by sensor 108, permitting sensation of both breath composition and environmental air composition.

Figure 4:
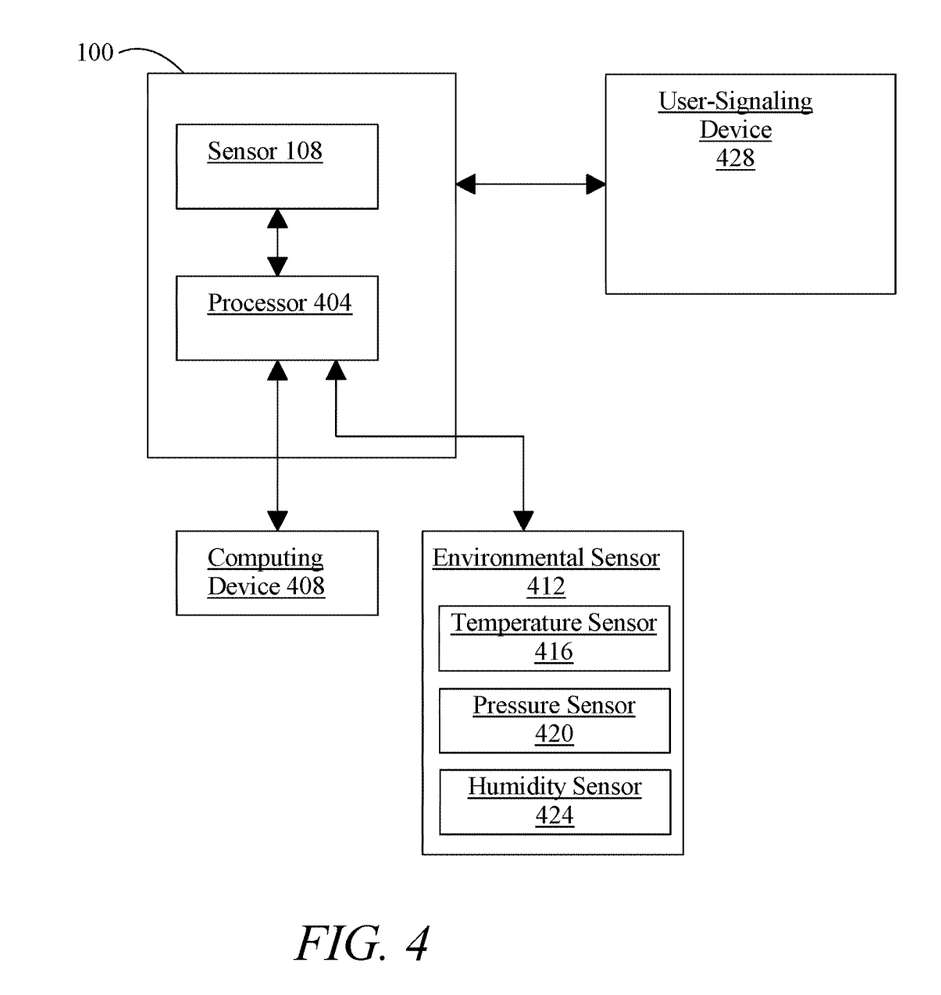
FIG. 4 is a block diagram illustrating an exemplary embodiment of a combined exhaled air and environmental gas sensor apparatus.

Referring now to FIG. 4, apparatus 100 includes a sensor 108. Sensor 108 is positioned within housing 104. Sensor 108 is configured to detect one or more quantities and/or percentages of gases. In an embodiment, sensor 108 is configured to detect a carbon dioxide level and generate sensor 108 outputs indicating detected carbon dioxide level. Sensor 108 may alternatively or additionally detect one or more gases, droplets, particulate elements, or the like, which may be indicative of health and/or physiological status of a person using mobile respiratory device 300 and/or apparatus 100, of environmental conditions that may affect such status, or both. Sensor 108 may be configured to detect a carbon dioxide level by detecting a level of a related compound detecting the carbon dioxide level as a function of the level of the related compound. A "related compound," as used in this disclosure, is a compound quantities, percentages, and/or concentrations of which may be used to predict quantities, percentages, and/or concentrations of carbon dioxide in one or more contexts, owing to statistical correlations between the two. For instance, and without limitation, quantities, percentages, and/or concentrations of carbon dioxide from sources such as humans and/or other animals may be proportional to quantities, percentages, and/or concentrations of $H_2$ (hydrogen) gas and/or volatile organic compounds. In an embodiment, a related compound may be more readily or accurately detected using an electrical component of a sensor 108. Sensor 108 may detect a quantity, percentage, and/or concentration of a related compound such as $H_2$, volatile organic compounds, or the like and calculating an associated level of $CO_2$. Sensor 108 may be configured to detect quantities, percentages, and/or concentrations of any other compound directly and/or by detection of a related compound and calculation of the quantities, percentages, and/or concentrations. Such a signal may be used to distinguish the influence of a human presence from other contaminants; for instance, in indoor environments, $H_2$ concentration may be related to $CO_2$ concentration as human breath contains significant concentrations of both, $CO_2$ (4%) and $H_2$ (10 ppm).

Still referring to FIG. 4, sensor 108 may be configured to detect quantities, percentages, and/or concentrations of hydrogen gas ($H_2$). Sensor 108 may be configured to sense quantities, percentages, and/or concentrations of one or more volatile organic compounds. A "volatile organic compound," as used in this disclosure, are organic compounds having high vapor pressure at room temperature. Volatile organic compounds may include without limitation, alcohols such as ethanol, isoprene, chlorofluorocarbons, benzine, methylene chloride, perchloroethylene, methyl tert-butyl ether (MTBE), and/or formaldehyde. Sensor 108 may be configured to detect a total volatile organic compound (tVOC) quantities, percentage, and/or concentration. "Total volatile organic compound," as used in this disclosure, is a total concentration of volatile organic compounds present simultaneously in the air. Sensor 108 may detect tVOC using a sensor 108 that is sensitive to sets of volatile organic compounds, a sensor 108 that is sensitive to each of a plurality of volatile organic compounds, and/or sensitive to one or more organic compounds having a quantities, percentages, and/or concentrations of which may be used to predict quantities, percentages, and/or concentrations of tVOC and/or components thereof. For instance, and without limitation, quantities, percentages, and/or concentrations of ethanol in air may be associated with quantities, percentages, and/or concentrations of other volatile organic compounds; sensor 108 may be configured to detect levels and/or quantities of ethanol and calculate tVOC using such detected quantities.

With continued reference to FIG. 4, sensor 108 may alternatively or additionally be configured to sense one or more hazardous gases, droplets, particulate matter or the like, including without limitation hazardous gases, droplets, particulate matter produced by indoor or outdoor air pollution sources, whether natural or anthropogenic, hazardous gases, droplets, particulate matter produced intentionally as an act of violence or war, or the like. Alternatively or additionally, sensor 108 may be configured to detect one or more diagnostically useful gases, droplets, particulate matter or the like, where a "diagnostically useful" gas, droplet, and/or element of particulate matter is defined as a gas, droplet, and/or element of particulate matter that provides information usable to determine a physiological state of a user, for instance as described in further detail below.

Still referring to FIG. 4, sensor 108 may function using any suitable technology, including without limitation a detector, defined as a circuit element that modifies a circuit parameter when exposed to a compound to be detected. For instance, and without limitation, sensor 108 may use a heating element to temperature of a heated metal-oxide detector, such as a tin-based component that changes resistance based on exposure to a compound to be detected; output may be fed to an operational amplifier, such as without limitation an operational amplifier configured to cover a measurement range of 8 orders of magnitude. Sensor 108 may include, for instance, a first such detector configured to detect $CO_2$ and/or a related compound and a second detector configured to detect tVOC and/or a representative compound such as ethanol as described above. Sensor 108 may include, without limitation, input and output ports, a microcontroller for performing calculations as described above, one or more registers and/or more memory elements such as without limitation random-access memory (RAM) such as block random-access memory (BRAM), flash memory, or the like. Sensor 108 may include one or more wireless transceivers or other devices for communication with other elements of apparatus 100, and/or may be wired to such elements. Sensor 108 may be connected to a power source such as a battery or other voltage source.

Alternatively or additionally, and still referring to FIG. 4, sensor 108 may include one or more sensors 108 and/or detectors operating according to one or more additional technologies, such as without limitation at least a chemical sensor 108, which may be based on polymer or heteropolysiloxane; chemical sensor 108 may be configured to detect concentrations of $CO_2$, estimated $CO_2$, tVOC, and/or any other element that may be detected by sensor 108 as above.

With continued reference to FIG. 4, apparatus 100 includes a processor 404 communicatively connected to the sensor 108. Processor 404 may include any processor 404 as described in this disclosure. Processor 404 may be incorporated in any computing device as described in this disclosure, and may include and/or be include in, without limitation, a microcontroller, microprocessor 404, digital signal processor 404 (DSP) and/or system on a chip (SoC) as described in this disclosure. Processor 404 may interface or communicate with one or more additional devices as described below in further detail via a network interface device. Network interface device may be utilized for connecting processor 404 to one or more of a variety of networks, and one or more devices. Examples of a network interface device include, but are not limited to, a network interface card (e.g., a mobile network interface card, a LAN card), a modem, and any combination thereof.

Still referring to FIG. 4, processor 404 may communicate with a computing device 408, which may include, for example, a computing device 408 or cluster of computing devices in a first location and a second computing device 408 or cluster of computing devices in a second location. Computing device 408 may include one or more computing devices dedicated to data storage, security, distribution of traffic for load balancing, and the like. Computing may distribute one or more computing tasks as described below across a plurality of computing devices of computing device 408, which may operate in parallel, in series, redundantly, or in any other manner used for distribution of tasks or memory between computing devices. Computing device 408 may be implemented using a "shared nothing" architecture in which data is cached at the worker, in an embodiment, this may enable scalability of system 100 and/or computing device 408. Computing device 408 may include without limitation a mobile and/or portable device, a device incorporated in a vehicle such as an aircraft, a computing device 408 incorporated in a wearable piece of equipment such as helmet or the like.

Processor 404 may be attached to housing 104, for instance by incorporation within housing 104; as a non-limiting example, processor 404 may be installed against sensor-bearing surface 112 or other portion of interior surface 204. Processor 404 may be attached to an exterior of housing 104. Processor 404 may be in another location not attached to or incorporated in housing 104. Processor 404 may be incorporated into and/or connected to one or more additional elements including any elements incorporating or connected to user signaling devices as described in further detail below. As an alternative to storage of one or more parameter values such as detected concentrations and/or levels of gas or the like and/or environmental parameters in memory, processor 404 may transmit the data to one or more remote storage mediums through one or more wired and/or wireless means.

With continued reference to FIG. 4, processor 404 may be communicatively connected to sensor 108. As used herein, a device, component, or circuit is "communicatively connected" where the device, component, or circuit is able to receive data from and/or transmit data to another device, component, or circuit. In an embodiment, devices are placed in communicative connection by electrically coupling at least an output of one device, component, or circuit to at least an input of another device, component, or circuit. Devices may further be placed in communicatively connection by creating an optical, inductive, or other coupling between two or more devices. Communicatively connected device may be placed in near field communication with one another. Two or more devices may be communicatively connected where the two or more devices are configured to send and/or receive signals to or from each other. Placement of devices in communicative connection may include direct or indirect connection and/or transmission of data; for instance, two or more devices may be connected or otherwise communicatively connected by way of an intermediate circuit. Placement of devices in communicative connection with each other may be performed via a bus or other facility for intercommunication between elements of a computing device 408 as described in further detail below. Placement of devices in communicative connection with each other may include fabrication together on a shared integrated circuit and/or wafer; for instance, and without limitation, two or more communicatively coupled devices may be combined in a single monolithic unit or module.

Still referring to FIG. 4, processor 404 may be communicatively connected to one or more additional elements such as without limitation an environmental sensor 412. As used in this disclosure, an environmental sensor 412 may be any sensor 108 configured to detect at least an environmental parameter, defined herein as a parameter describing non-physiological data concerning user or surroundings of user. At least an environmental sensor 412 may include at least a motion sensor 108, including without limitation one or more accelerometers, gyroscopes, magnetometers, or the like; at least a motion sensor 108 may include an inertial measurement unit (IMU). At least an environmental sensor 412 may include at least a temperature sensor 416. At least an environmental sensor 412 may include at least a barometric sensor. At least an environmental sensor 412 may include a pressure sensor 420, for instance to detect air or water pressure external to user. At least an environmental sensor 412 may include a humidity and/or relative humidity sensor 424.

Continuing to refer to FIG. 4, processor 404 may be communicatively connected to at least a user-signaling device 428. In an embodiment, at least a user-signaling device 428 may be incorporated in apparatus 100; for instance, at least a user-signaling device 428 may be attached to or incorporated in housing 104. Alternatively or additionally, apparatus 100 may communicate with a user-signaling device 428 that is not incorporated in apparatus 100, such as a display, headset, or other device provided by a third party or the like, which may be communicatively connected with processor 404. User-signaling device 428 may be or incorporate a device for communication with an additional user-signaling device 428 such as a vehicle display and/or helmet avionics; for instance, user-signaling device 428 may include a wireless transmitter or transponder communicatively connected with such additional devices.

Continuing to refer to FIG. 4, at least a user-signaling device 428 may include any device capable of transmitting an audible, tactile, or visual signal to a user when triggered to do so by processor 404. In an embodiment, and as a non-limiting example, at least a user-signaling device may include a bone-conducting transducer in vibrational contact with a bone beneath the exterior body surface. A bone-conducting transducer, as used herein, is a device or component that converts an electric signal to a vibrational signal that travels through bone placed in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing 104 in a position placing it in contact with a user's bone; for instance, where housing 104 includes or is incorporated in an ear cup, housing 104 may place bone-conducting transducer in contact with user's skull just behind the ear, over the sternocleidomastoid muscle. Likewise, where housing 104 includes a headset, mask, or helmet, housing 104 may place bone-conducting transducer in contact with a portion of user's skull that is adjacent to or covered by headset, mask, or helmet.

Still referring to FIG. 4, at least a user-signaling device 428 may further include an audio output device. Audio output device may include any device that converts an electrical signal into an audible signal, including without limitation speakers, headsets, headphones, or the like. As a non-limiting example, audio output device may include a headset speaker of a headset incorporating or connected to apparatus 100, a speaker in a vehicle user is traveling in, or the like. At least a user-signaling device 428 may include a light output device, which may be any device that converts an electrical signal into visible light; light output device may include one or more light sources such as LEDs, as well as a display, which may be any display as described below. At least a user-signaling device 428 may include a vehicular display; at least a vehicular display may be any display or combination of displays presenting information to a user of a vehicle user is operating. For instance, at least a vehicular display may include any combination of audio output devices, light output devices, display screens, and the like in an aircraft flight console, a car dashboard, a boat dashboard or console, or the like; processor 404 may be communicatively connected with vehicular display using any form of communicative connection described above, including without limitation wired or wireless connection. At least a user-signaling device 428 may include a helmet display; helmet display may include any visual, audio, or tactile display incorporated in any kind of helmet or headgear, which may be communicatively connected with processor 404 according to any form of communicative connection as described above.

Further referring to FIG. 4, any of the above user-signaling device 428 and/or signals may be used singly or in combination; for instance, a signal to user may include an audio signal produced using a bone-conducting transducer, a verbal message output by an audio output device, and a visual display of an image or text indicating an output. Persons skilled in the art, upon reviewing the entirety of this disclosure, will be aware of various combinations of signaling means and/or processes that may be employed to convey a signal to user. In an embodiment, in addition to transmitting a signal to user-signaling device 428, processor 404 may transmit a signal to one or more automated vehicular controls or other systems to alleviate one or more environmental parameters contributing to physiological alarm condition.

Still referring to FIG. 4, processor 404 may be designed and/or configured to perform any method, method step, or sequence of method steps in any embodiment described in this disclosure, in any order and with any degree of repetition. For instance, processor 404 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 404 may perform any step or sequence of steps as described in this disclosure in parallel, such as simultaneously and/or substantially simultaneously performing a step two or more times using two or more parallel threads, processor 404 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 4, processor 404 is configured to have a breath analysis mode and an environmental analysis mode. In breath analysis mode, processor 404 is configured to detect one or more concentrations of compounds exhaled by a person wearing mobile respiratory device 300, such as without limitation concentrations of exhaled $CO_2$, exhaled volatile organic compounds and/or tVOC, or the like; processor 404 may then make one or more determinations based on the detected concentrations as described in further detail below. In environmental analysis mode, processor 404 is configured to detect one or more concentrations of compounds in environment surrounding a person, such as $CO_2$ levels, VOC levels, tVOC levels, or the like; processor 404 may then make one or more determinations based on the detected concentrations as described in further detail below.

Still referring to FIG. 4, processor 404 is configured to receive a plurality of sensor 108 outputs from the sensor 108; processor 404 may periodically sample and/or poll data from at least a sensor 108; in a non-limiting example, data may be sampled 75 times per second. In an embodiment, alarm is generated upon detection of any signal at all from sensor 108; for instance, sensor 108 may be configured only to signal processor 404 upon detection of a problematic or otherwise crucial situation. Plurality of sensor 108 outputs may include outputs representing concentrations of compounds as sensed by sensor 108, including without limitation concentrations of $CO_2$, tVOC, $H_2$, or the like.

With continued reference to FIG. 4, processor 404 is configured to match the plurality of sensor 108 outputs to mode parameter profile. A "mode parameter profile" as used in this disclosure is a set of sensor 108 readings indicative of either exhalation of breath through exhaust port or a lack thereof. For instance, and without limitation, a sequence of measured $CO_2$ and/or tVOC amounts may follow a pattern that matches an exhalation of breath; processor 404 may be programmed to recognize such a pattern and identify the pattern as indicative of a current exhalation of breath. Similarly, another sequence of sensor 108 outputs may be consistent with an absence of exhalation past sensor 108, which may indicate that a person wearing mobile respiratory device 300 is inhaling, and/or that the person has removed or deactivated mobile respiratory device 300, which processor 404 may recognize and switch as a result to environmental analysis mode.

Still referring to FIG. 4, processor 404 may be configured to identify a mode parameter profile using a machine-learning model, which may be generated by processor 404 and/or an additional computing device 408 using a machine-learning algorithm. A "machine learning process," as used in this disclosure, is a process that automatedly uses a body of data known as "training data" and/or a "training set" to generate an algorithm that will be performed by a computing device 408/module to produce outputs given data provided as inputs; this is in contrast to a non-machine learning software program where the commands to be executed are determined in advance by a user and written in a programming language.

Continuing to refer to FIG. 4, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and still referring to FIG. 4, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by processor 404 and/or other device to train a machine-learning model may correlate any input data as described in this disclosure to any output data as described in this disclosure. As a non-limiting illustrative example training data may include a plurality of sensor 108 data sequences and correlated exhalations and/or absences thereof, such that training data may be used to train a machine-learning model to distinguish between a mode parameter profile associated with an exhalation and a mode parameter profile associated with a lack of exhalation.

Further referring to FIG. 4, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning model may include a mode classifier, which may be a classifier configured to identify a mode based on a mode parameter set. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 408 104 and/or another device may generate a classifier using a classification algorithm, defined as a processes whereby a computing device 408 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 4, classification algorithm may include a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Still referring to FIG. 4, generating k-nearest neighbors algorithm may include generating a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 4, processor 404 may be configured to detect a breath as a function of the received sensor 108 outputs. Breath may be detected, without limitation, using mode classifier, which may detect one or more elevated levels of $CO_2$, related compounds, volatile organic compounds, tVOC or the like associated with an exhalation; breath detection may include detection of a sequence of such levels and intervening reductions and/or steady states of such $CO_2$, related compounds, volatile organic compounds, tVOC or the like. In an embodiment, processor 404 may be configured to switch to breath analysis mode during a detected breath. Processor 404 may be configured to switch to environmental analysis mode after a detected breath. For instance, and without limitation, processor 404 may detect a mode parameter profile associated with a lack of exhalation, and wait a preconfigured period of time, as measured for instance by counting clock cycles or the like, before recording environmental parameters such as cabin $CO_2$, tVOC, or the like; a pause prior to measurement of environmental parameters may permit exhaled gases, droplets, or the like to dissipate, permitting a more accurate measurement of ambient levels of measured substances. Processor 404 may determine that mobile respiratory device 300 is being worn by a person when exhalations are detected iteratively above a threshold regularity and/or frequency over a period of time; lack of such detection may cause processor 404 to determine that mobile respiratory device 300 has been disabled and/or removed from the person, which may result in differing analysis as described in further detail below.

Still referring to FIG. 4, processor 404 may be configured to calibrate sensor 108 to a calibration setting. Calibration setting may be a setting used to calibrate sensor 108 to known concentrations and/or quantities of $CO_2$, related compounds, volatile organic compounds, tVOC, or other substances to be sensed by sensor 108. Known concentrations and/or quantities may be determined beforehand, for instance in a laboratory or test facility setting, a sensor 108 that has already bee calibrated and/or a sensor 108 having a high accuracy level such as a light spectroscopy sensor 108, such as a NDIR (nondispersive infrared), in which $CO_2$ or other substance of and/or containing gas is pumped or diffused into a light tube, interference (wavelength) filter and light detector such as an infrared detector, and absorption characteristics are measured by dips in transmitted light of one or more frequencies. Calibration relationships between known levels of compounds to be sensed and corresponding sensor 108 outputs may be stored in memory of processor 404, which may implement, for instance and without limitation, a look up table to determine levels of sensed substances based on sensor 108 outputs.

In an embodiment, and with further reference to FIG. 4, processor 404 may be configured to select the calibration setting from a plurality of candidate calibration settings as a function of at least an environmental parameter. At least an environmental parameter may be any parameter and/or combination of parameters detectable by an environmental sensor 412 as described above. At least an environmental parameter may include one or more parameters that can affect sensor 108 readings, such as humidity, temperature, and/or air pressure. Sensor 108 may self-correct for variation in such environmental parameters if the environmental parameters are input to sensor 108; alternatively or additionally, computing device 408 may use different calibration settings for different levels of environmental parameters and/or combinations thereof; such levels may be set in a test facility and/or measured in combination with sensor 108 outputs and known levels of substances to be sensed. Processor 404 may compare at least an environmental parameter to one or more values and/or ranges of values to determine which calibration setting to use. Thus, for instance, a first calibration setting may be used for a pressure of approximately 1 atm, a relative humidity level of 30%, and a temperature of 24 degrees Celsius, while a second calibration setting may be used for a pressure of approximately 0.5 atm, a relative humidity level of 10%, and a temperature of 5 degrees Celsius; persons skilled in the art, upon reviewing the entirety of this disclosure, will be aware of various variations in environmental parameters and calibration settings that may be employed.

Alternatively or additionally, and still referring to FIG. 4, processor 404 may use a calibration function of environmental parameters and sensor 108 outputs to determine levels of one or more sensed substances. Calibration function, which may have a form of a linear and/or polynomial function of environmental parameters and sensor 108 outputs, may enable processor 404 to determine accurate concentrations of sensed substances across a continuous range of environmental parameter and sensor 108 output values. In an embodiment, training data may be developed using one or more recorded calibration settings as described above, and then used to train a machine-learning model including a calibration function; training may be performed using a regression algorithm and produce a regression model including calibration function. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms used to produce calibration function may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression.

Still referring to FIG. 4, processor 404 may be configured to detect one or more problematic situations and alert a person using apparatus 100 and/or mobile respiratory device 300 as a function of the detection; processor 404 may alert user by utilizing any user signaling device or combination of user signaling device. For instance and without limitation, processor 404 may be configured to detect a dangerous carbon dioxide level and output a user alert as a function of the detection; alert may, for instance, instruct a user who is not wearing and/or using mobile respiratory device 300, which may be detected as described above, to start using mobile respiratory device 300 to receive oxygen and/or exclude $CO_2$. Similarly, detection of one or more environmental hazards such as toxic gas and/or droplets or the like may cause processor 404 to alert user to utilize mobile respiratory device 300 and/or to take other actions to escape environment and/or to alleviate the detected hazardous condition.

With continued reference to FIG. 4, when in breath mode processor 404 may detect a user condition as a function of plurality of sensor 108 outputs. User condition may include any condition that may be associated with any detected concentration of any chemical in breath, and/or any pattern of breathing activity. For instance, and without limitation, detection of a user condition may include detection of hypocapnia, defined as a lower level of carbon dioxide in blood and/or tissues of the user; in an embodiment, detection of low $CO_2$ levels in an exhaled breath and/or a series of exhaled breaths may be interpreted by processor 404 as indicating hypocapnia. Processor 404 may compare degree of hypocapnia and/or level of breath $CO_2$ to a preconfigured threshold associated with severe hypocapnia, defined as a degree of hypocapnia sufficient to create a risk of disorientation and/or unconsciousness such as a "shallow water blackout"; a warning may be issued to user via user signaling device indicating risk of severe hypocapnia, and/or including one or more instructions for user to take measures to counteract hypocapnia, such as slower, deeper breathing. User condition may include hypercapnia, defined as an excess of $CO_2$ in user's blood and/or tissues; in an embodiment, detection of high $CO_2$ levels in an exhaled breath and/or a series of exhaled breaths may be interpreted by processor 404 as indicating hypercapnia. Processor 404 may compare degree of hypercapnia and/or level of breath $CO_2$ to a preconfigured threshold associated with severe hypercapnia, defined as a degree of hypercapnia sufficient to create a risk of disorientation and/or unconsciousness; a warning may be issued to user via user signaling device indicating risk of severe hypercapnia, and/or including one or more instructions for user to take measures to counteract hypercapnia, such as more rapid breathing.

Still referring to FIG. 4, processor 404 in breath mode may detect a user condition based on detected changes in ketone or volatile organic compound emission by user, where greater ketone and/or volatile organic compound emission may indicate a elevated degree of fatigue, which may be used as described above, and/or a more severe degree of hypoxemia for a given blood oxygen saturation level and/or heart rate. In an embodiment, a user may emit ketones in greater quantities when undergoing some forms of physiological stress, including without limitation hypoglycemia resulting from fasting or overwork, which sometimes results in a metabolic condition known as ketosis. As a result, detections of higher quantities of ketones may indicate a high degree of exhaustion or low degree of available energy; this may be associated with a lessened ability to cope with other physiological conditions and/or parameters that may be detected by or using sensor 108, such as hypoxemia, and/or environmental stressors such as high altitude or G-forces. Such associations may be detected or derived using data analysis and/or machine learning as described in further detail below.

Further referring to FIG. 4, processor 404 may detect user condition as a function of one or more breath patterns. For instance, a speed of breath may be detected, where rapid breaths in excess of a preconfigured threshold quantity indicative of breath speed may indicate hyperventilation and/or shallow breathing; levels of detected substances in breath may be used to determine whether user is engaging in rapid, deep breaths associated with hyperventilation or rapid shallow breaths. Hypoventilation may be detected based on a slower rate of breaths than a preconfigured threshold quantity.

Still referring to FIG. 4, detection of user condition may include detection using one or more machine-learning models and/or classifiers as described above. For instance, and without limitation apparatus 100, other apparatus 100es, and/or testing facilities as described above, may collect relationships between breath patterns and/or concentrations or other levels of one or more detected substances and user conditions; such relationships, and/or other data including such relationships, may be used as training data to train a machine-learning model, classifier, or the like to recognize input patterns associated with user conditions, which processor 404 may use to identify one or more user conditions as a result of a detected pattern.

Figure 5:
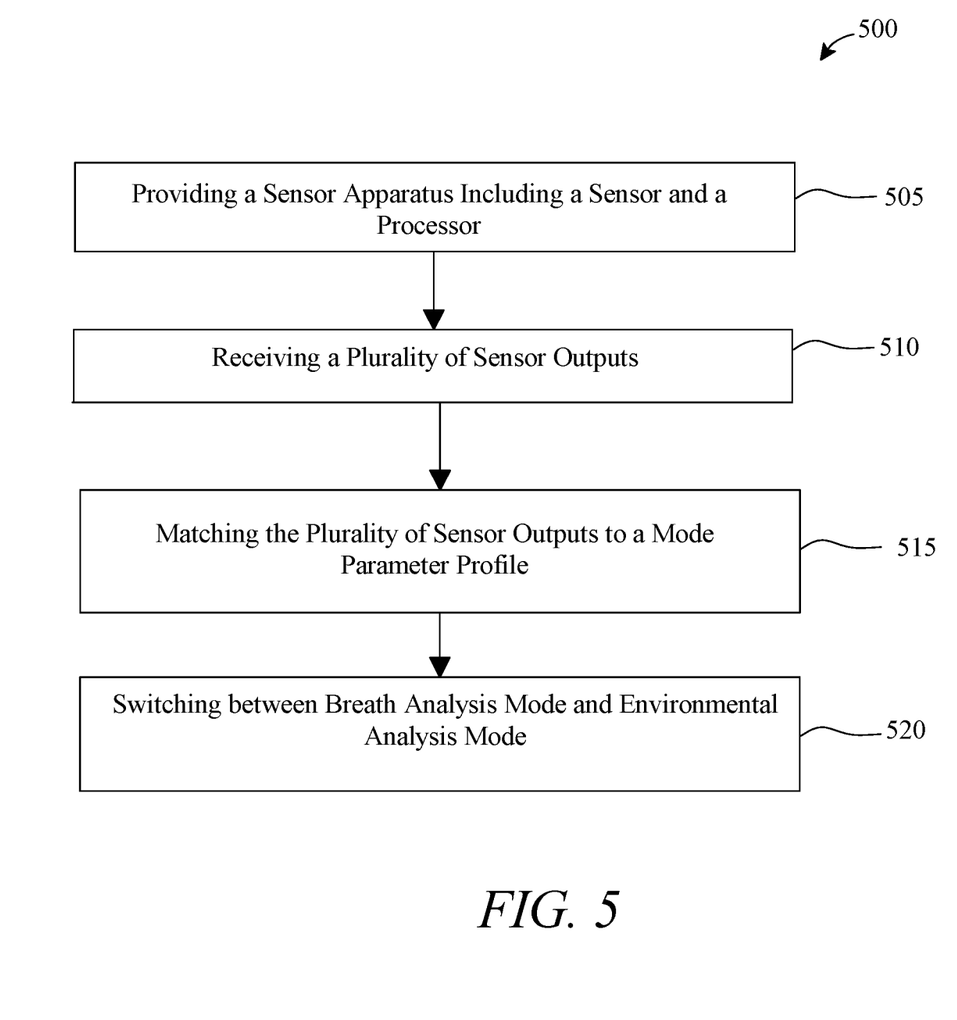
FIG. 5 is a flow diagram illustrating an exemplary embodiment of a method of substance detection using a combined exhaled air and environmental gas sensor apparatus.

Referring now to FIG. 5, an exemplary embodiment of a method 500 of substance detection using a combined exhaled air and environmental gas sensor 108 apparatus 100 is illustrated. At step 505, a sensor 108 apparatus 100 is provided. Sensor 108 apparatus 100 may include any sensor 108 apparatus 100 as described above in reference to FIGS. 1-4. For instance, and without limitation, sensor 108 apparatus 100 may be attached to a respiratory exhaust port. Sensor 108 apparatus 100 may include a sensor 108 and a processor 404 communicatively connected to the sensor 108. Processor 404 may have a breath analysis mode and an environmental analysis mode, for instance as described above.

At step 510, and still referring to FIG. 5, processor 404 receives a plurality of outputs from sensor 108; this may be implemented, without limitation, as described above in reference to FIGS. 1-4. Plurality of sensor 108 outputs may include, without limitation, a plurality of $CO_2$ levels, a plurality of tVOC readings, and/or one or more readings of amounts, percentages, and/or concentrations of one or more substances, whether detected directly and/or calculated based on related and/or representative substances as described above.

With continued reference to FIG. 5, at step processor 404 matches plurality of sensor 108 outputs to a mode parameter profile; this may be implemented in any manner described above in reference to FIGS. 1-4. Matching may include comparison to one or more stored patterns, use of machine-learning models and/or classifiers, or the like.

Still referring to FIG. 5, processor 404 switches between breath analysis mode and environmental analysis mode as a function of mode parameter profile, for instance as described above in reference to FIGS. 1-4. Processor 404 may detect one or more user conditions as described above. Processor 404 may detect one or more hazardous environmental conditions as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
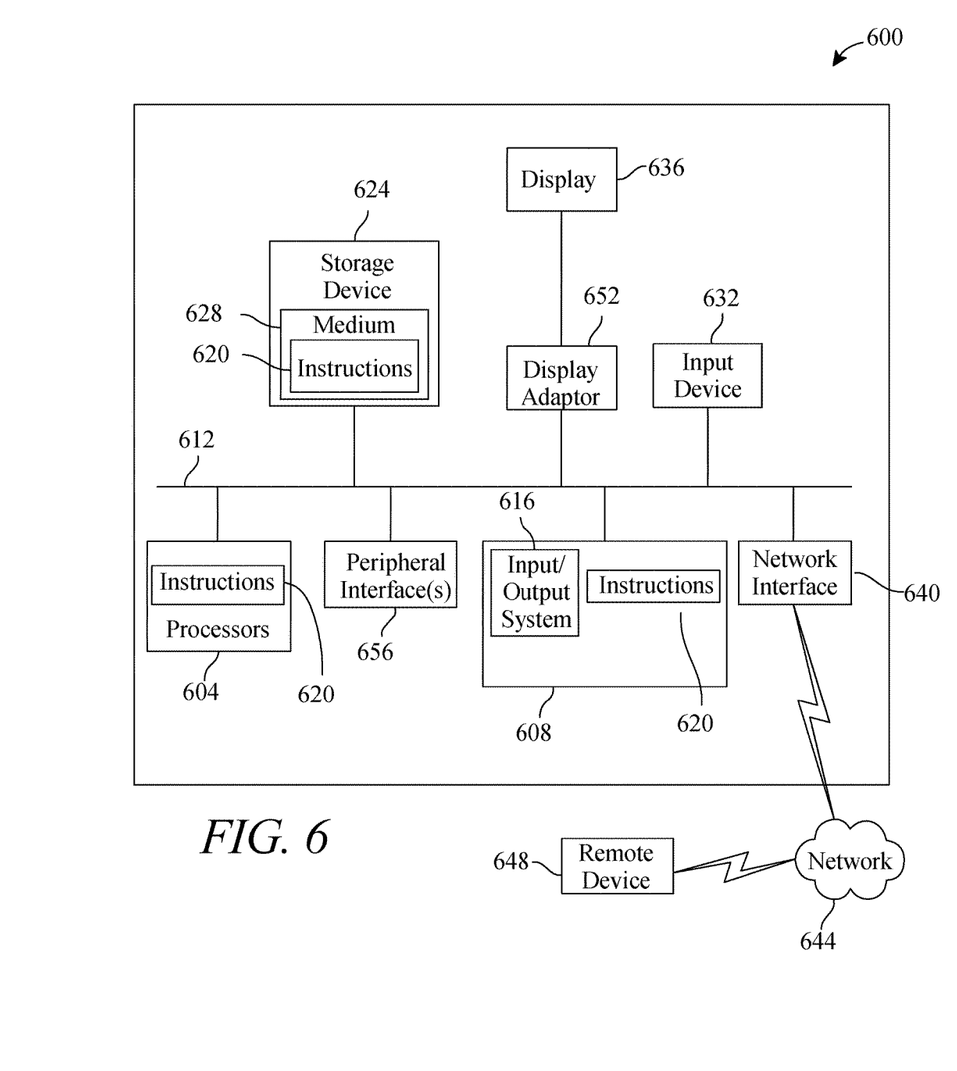
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A combined exhaled air and environmental gas sensor apparatus for mobile respiratory equipment, the apparatus comprising:
   a housing, wherein the housing further comprises:
      a port aperture;
      a connector configured to attach the port aperture to a respiratory exhaust port;
      at least an ambient aperture connecting to an exterior environment; and
      a plenum comprising the port aperture and the at least an ambient aperture, wherein the plenum is configured to permit free flow of exhaled air from the port aperture and environmental gas from the exterior environment by way of the at least an ambient aperture;
   a sensor positioned within the plenum, the sensor configured to detect a carbon dioxide level of gas within the plenum and generate a plurality of sensor outputs indicating detected carbon dioxide level;
   a processor communicatively connected to the sensor, the processor, including a memory, is configured to operate in a breath analysis mode and an environmental analysis mode;
      receive the plurality of sensor outputs from the sensor;
      match the plurality of sensor outputs to a mode parameter profile; and
      switch from the breath analysis mode to the environmental analysis mode as a function of the mode parameter profile;
      wherein the processor in the environmental analysis mode is configured to:
         measure, by the sensor, the carbon dioxide level of the environmental gas; and
      wherein the processor in the breath analysis mode is configured to:
         measure, by the sensor, the carbon dioxide level of the exhaled gas.

2. The apparatus of claim 1, wherein the housing includes a sensor-bearing surface, and the sensor is attached to the sensor-bearing surface.

3. The apparatus of claim 2, wherein the sensor-bearing surface is located opposite the port aperture.

4. The apparatus of claim 1, wherein the sensor is configured to detect the carbon dioxide level by:
   detecting a level of a related compound; and
   detecting the carbon dioxide level as a function of the level of the related compound.

5. The apparatus of claim 1, wherein the sensor is configured to detect a level of at least a volatile organic compound.

6. The apparatus of claim 1, wherein the sensor is configured to detect a total volatile organic compound level.

7. The apparatus of claim 1, wherein the processor is further configured to detect a breath as a function of the received sensor outputs.

8. The apparatus of claim 7, wherein the processor is further configured to switch to breath analysis mode during the detected breath.

9. The apparatus of claim 7, wherein the processor is further configured to switch to environmental analysis mode after the detected breath.

10. The apparatus of claim 1, wherein the processor is configured to calibrate the sensor to a calibration setting.

11. The apparatus of claim 10, further comprising an environmental sensor located at least partially within the exterior environment, wherein the environmental sensor is configured to detect at least an environmental parameter; and wherein the processor is configured to select the calibration setting from a plurality of candidate calibration settings as a function of the at least an environmental parameter.

12. The apparatus of claim 11, wherein the at least an environmental parameter includes a temperature.

13. The apparatus of claim 11, wherein the at least an environmental parameter includes a pressure.

14. The apparatus of claim 11, wherein the at least an environmental parameter includes a humidity level.

15. The apparatus of claim 1 further comprising an environmental sensor configured to detect at least an environmental parameter.

16. The apparatus of claim 1, wherein the processor is further configured to detect and output a user alert as a function of the detection.

17. The apparatus of claim 1, wherein the processor is further configured to detect a user condition.

18. The apparatus of claim 17, wherein the user condition includes hypocapnia.

19. The apparatus of claim 17, wherein the user condition includes fatigue.

20. The apparatus of claim 1, wherein switching from the breath analysis mode to the environmental analysis mode comprises:
   determining, as a function of the mode parameter profile, a breath has occurred; and
   switching from the breath analysis mode to the environmental analysis mode after a preconfigured amount of time from when the breath occurred.

* * * * *